US009086351B1

United States Patent
D'Onofrio et al.

(10) Patent No.: US 9,086,351 B1
(45) Date of Patent: Jul. 21, 2015

(54) FIXTURE FOR SYSTEM-LEVEL GLOVE TESTING OF CONTACT PERMEATION

(71) Applicant: U.S. Army Edgewood Chemical Biological Center, APG, MD (US)

(72) Inventors: Terrence G. D'Onofrio, Bel Air, MD (US); Richard D. Wallace, III, Bel Air, MD (US); Brian K. MacIver, Middle River, MD (US)

(73) Assignee: The United States of America as Represented by the Secretary of the Army, Washington, DC (US)

( * ) Notice: Subject to any disclaimer, the term of this patent is extended or adjusted under 35 U.S.C. 154(b) by 317 days.

(21) Appl. No.: 13/827,891

(22) Filed: Mar. 14, 2013

(51) Int. Cl.
    *G01N 15/08* (2006.01)
(52) U.S. Cl.
    CPC .......... *G01N 15/082* (2013.01); *G01N 15/0806* (2013.01)
(58) Field of Classification Search
    CPC .. G01N 15/08; G01N 15/0806; G01N 15/082
    See application file for complete search history.

(56) References Cited

U.S. PATENT DOCUMENTS

| | | | | | |
|---|---|---|---|---|---|
| 4,918,981 | A | * | 4/1990 | Gore | 73/76 |
| 4,961,339 | A | * | 10/1990 | Kleis et al. | 73/73 |
| 5,073,482 | A | * | 12/1991 | Goldstein | 435/5 |
| 5,493,899 | A | * | 2/1996 | Beck et al. | 73/40.7 |
| 5,659,130 | A | * | 8/1997 | Chung et al. | 73/64.47 |
| 5,824,882 | A | * | 10/1998 | Griebel et al. | 73/38 |
| 6,204,669 | B1 | * | 3/2001 | Beard et al. | 324/557 |
| 6,234,005 | B1 | * | 5/2001 | Han et al. | 73/28.01 |
| 6,993,956 | B2 | * | 2/2006 | Bouten et al. | 73/40 |
| 7,117,720 | B2 | * | 10/2006 | Bouten et al. | 73/40 |
| 9,021,865 | B1 | * | 5/2015 | D'Onofrio | 73/38 |
| 2005/0026294 | A1 | * | 2/2005 | Barber | 436/8 |
| 2006/0130559 | A1 | * | 6/2006 | Doehla et al. | 73/37 |

\* cited by examiner

*Primary Examiner* — John Fitzgerald
(74) *Attorney, Agent, or Firm* — Ulysses John Biffoni

(57) ABSTRACT

A system and method for testing contact permeation of a glove using a mannequin hand having fingers and a thumb. A hand cradle supports the mannequin hand with the palm of the hand facing away from the hand cradle. A patterned weight block applies pressure to the palm, fingers, and thumb of the hand. A weight block is placed on the patterned weight block and the whole assembly is placed in an air tight containment box. The mannequin hand is covered with a protection layer, a sorptive glove layer, and a test glove. The test glove is contaminated with the chemical of interest. Pressure is applied to the palm, fingers, and thumb of the test glove, and the contaminant that permeates through the test glove into the sorptive glove layer is collected and measured.

18 Claims, 4 Drawing Sheets

FIXTURE FOR SYSTEM-LEVEL GLOVE TESTING OF CONTACT PERMEATION

GOVERNMENT INTEREST

The invention described herein may be manufactured, used, and licensed by or for the United States Government.

TECHNICAL FIELD OF THE INVENTION

The present invention relates generally to a fixture and test method to test chemical protection efficiency of complete gloves. More specifically, the present invention relates to a fixture and test method for quantifying permeation breakthrough mass in a contact scenario.

BACKGROUND OF THE INVENTION

Permeation testing has traditionally focused on the use of swatches to measure breakthrough time or total cumulative mass of breakthrough at a specified time. Such an approach is appropriate for testing materials; however, these fixtures are limited to flat swatches.

Previous efforts have shown the need for contact testing to measure the contamination level on the underside of a protective material. While vapor methods for whole gloves have been developed, they may underestimate the breakthrough potential for low-volatility compounds (pesticides and chemical warfare agents), which pose a greater hazard from contact uptake into the skin, as opposed to vapor exposure.

SUMMARY OF THE INVENTION

According to an embodiment of the present invention, a system for testing contact permeation of a glove is disclosed. The system includes a mannequin hand with fingers and a thumb. A hand cradle adapted to contact a back surface of the mannequin hand and the fingers to stabilize the hand with a palm of the hand facing outward away from the hand cradle. A patterned weight block shaped to fit onto the palm of the mannequin hand for applying pressure to the palm, fingers, and thumb of the hand. A weight block is disposed on the outer surface of the patterned weight block. An air tight containment box receives the mannequin hand supported by the hand cradle and having the patterned weight block on the palm of the mannequin hand and the weight block disposed on the outer surface of the patterned weight block.

Further, according to an embodiment of the present invention, a method for testing contact permeation of a contaminant through a glove includes providing a mannequin hand with fingers and a thumb. A protective layer constructed of a material selected from the group consisting essentially of nitrile, butyl, neoprene, or other glove material that is appropriate for the containment of the contaminant being tested is placed over the mannequin hand. A sorptive glove layer is placed over the protective glove to capture the contamination through a test glove. A test glove covered with contaminant is placed over the sorptive glove layer. Pressure is applied to the palm, fingers, and thumb of the test glove. The contaminant that permeates through the test glove in the sorptive glove layer is collected and analyzed.

BRIEF DESCRIPTION OF THE DRAWINGS

The structure, operation, and advantages of the present invention will become further apparent upon consideration of the following description taken in conjunction with the accompanying figures (FIGs.). The figures are intended to be illustrative, not limiting. Certain elements in some of the figures may be omitted, or illustrated not-to-scale, for illustrative clarity. The cross-sectional views may be in the form of "slices", or "near-sighted" cross-sectional views, omitting certain background lines which would otherwise be visible in a "true" cross-sectional view, for illustrative clarity.

In the drawings accompanying the description that follows, both reference numerals and legends (labels, text descriptions) may be used to identify elements. If legends are provided, they are intended merely as an aid to the reader, and should not in any way be interpreted as limiting.

DETAILED DESCRIPTION OF THE PREFERRED EMBODIMENTS

Figure 1:
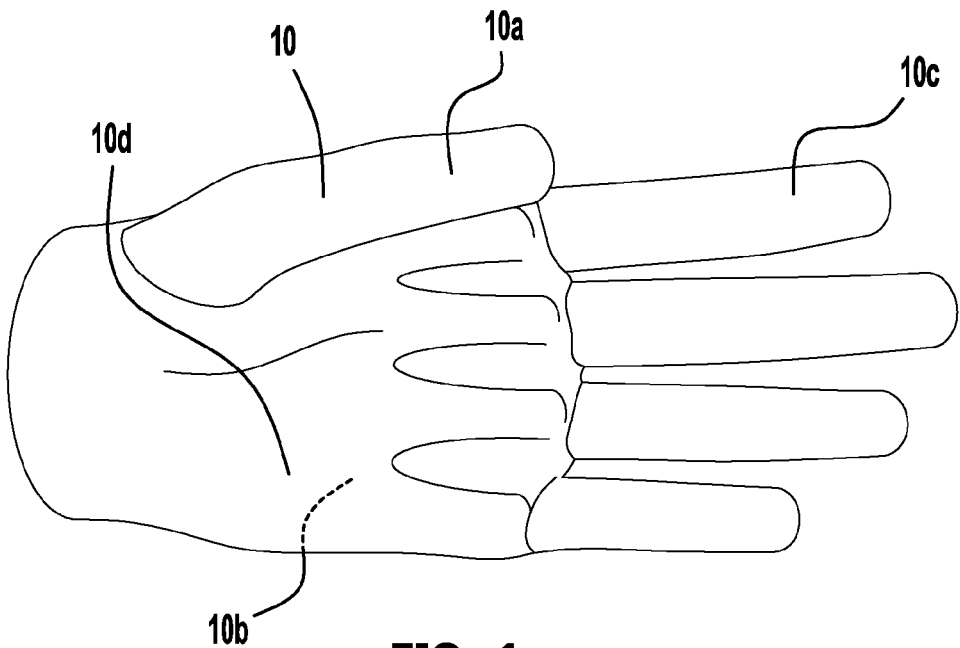
FIG. 1 is a top, three dimensional view of a mannequin hand, in accordance with the present invention.

In the description that follows, numerous details are set forth in order to provide a thorough understanding of the present invention. It will be appreciated by those skilled in the art that variations of these specific details are possible while still achieving the results of the present invention. Well-known processing steps are generally not described in detail in order to avoid unnecessarily obfuscating the description of the present invention.

In the description that follows, exemplary dimensions may be presented for an illustrative embodiment of the invention. The dimensions should not be interpreted as limiting. They are included to provide a sense of proportion. Generally speaking, it is the relationship between various elements, where they are located, their contrasting compositions, and sometimes their relative sizes that is of significance.

In the drawings accompanying the description that follows, often both reference numerals and legends (labels, text descriptions) will be used to identify elements. If legends are provided, they are intended merely as an aid to the reader, and should not in any way be interpreted as limiting.

The improved embodiment for permeation testing of as glove is disclosed. The permeation testing measures the time or total cumulative mass of breakthrough at a specified time. The application to a finished article or glove system enables the testing of regions otherwise hard to reach, such as between the fingers of the glove.

It should be noted that while methods for measuring the contamination level of vapors on the underside of a protective material forming a glove have been developed, they may underestimate the breakthrough potential for low-volatility compounds (pesticides and chemical warfare agents), which pose a greater hazard from contact than vapor uptake into the skin.

Therefore, the method disclosed herein tests the whole glove using contact testing to obtain a true measure of protection of the protective material of a glove in a contact scenario.

To test a glove, a mannequin hand 10 is constructed of a material such as plastic or nylon, such as by rapid prototyping. Referring to FIG. 1, there is shown a top, plan view of a left mannequin hand 10 with a thumb 10a, a back surface 10b, fingers 10c, and a palm 10d.

Figure 2:
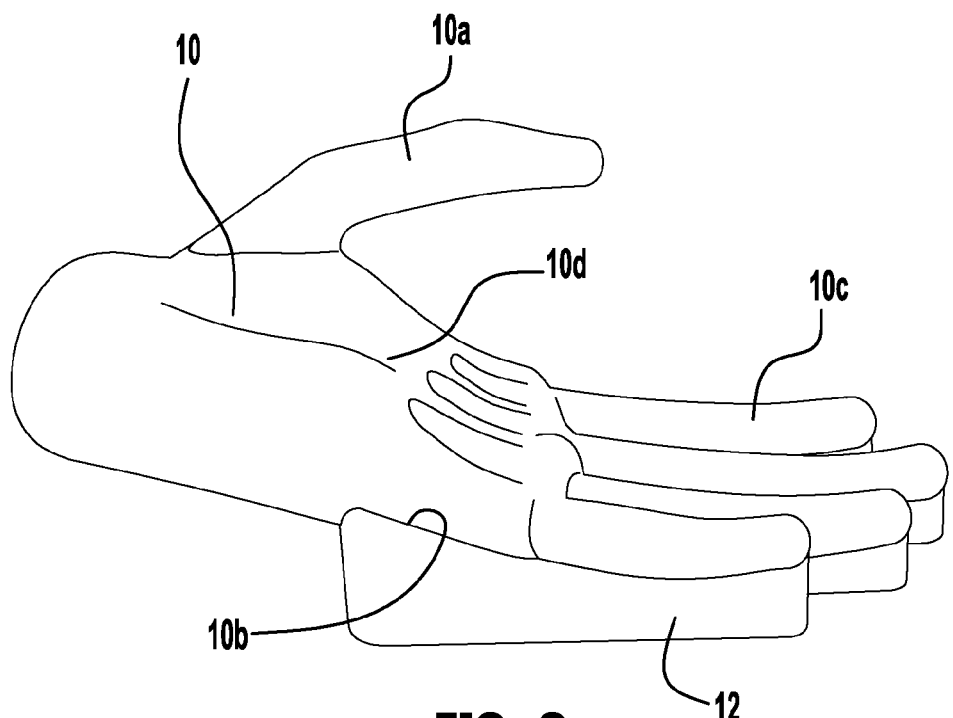
FIG. 2 is a side, three dimensional view of a mannequin hand supported on a cradle, in accordance with the present invention.

As shown in FIG. 2, a hand cradle 12 is manufactured of a material, such as plastic or nylon, such as by rapid prototyping. The hand cradle 12 is designed to contact the back surface 10b of the mannequin hand 10 and the fingers 10c so as to securely hold and stabilize the hand 10 with the palm 10d facing upward away from the hand cradle 12.

Figure 3A:
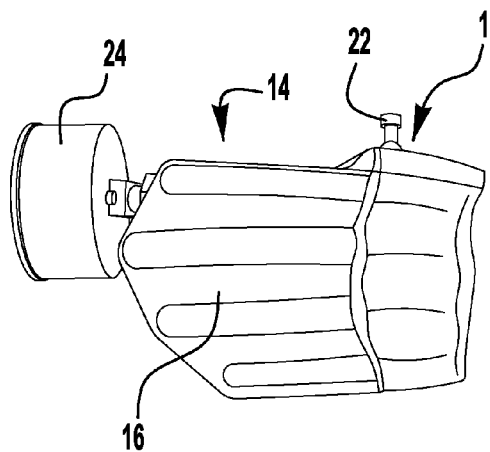
FIG. 3A is a top, three dimensional view of a weight block, in accordance with the present invention.
Figure 3B:
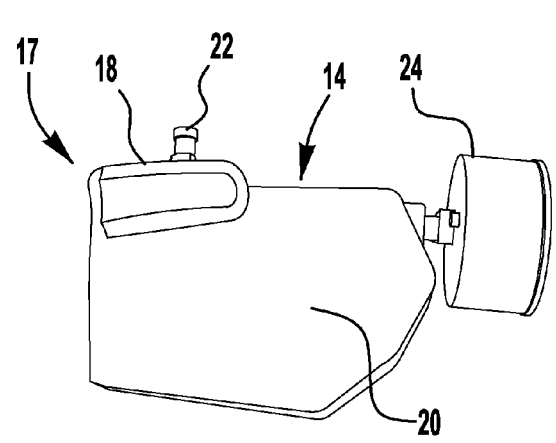
FIG. 3B is a bottom, three dimensional view of a weight block, in accordance with the present invention.

As shown in FIGS. 3A and 3B, there is provided is a patterned weight block 14 designed to fit the shape of the mannequin hand 10 and to apply pressure to the palm 10d, the fingers 10c, and the thumb 10a. Referring to FIG. 3A, the patterned weight block 14 has an inner surface 16 that is shaped to fit snuggly against the contours of the palm 10d and the fingers 10c of mannequin hand 10. A pressure system 17 including a rubber expansion chamber 18 that is provided on the outer surface 20 of the patterned weight block 14. The expansion chamber 18 of pressure system 17 can be inflated though the valve stem 22 to a desired pressure which is determined by a pressure gauge 24. As discussed hereinafter, the expansion chamber 18 is disposed between the thumb 10a of the mannequin hand 10 and the outer surface 20 of the patterned weight block 14.

Figure 4:
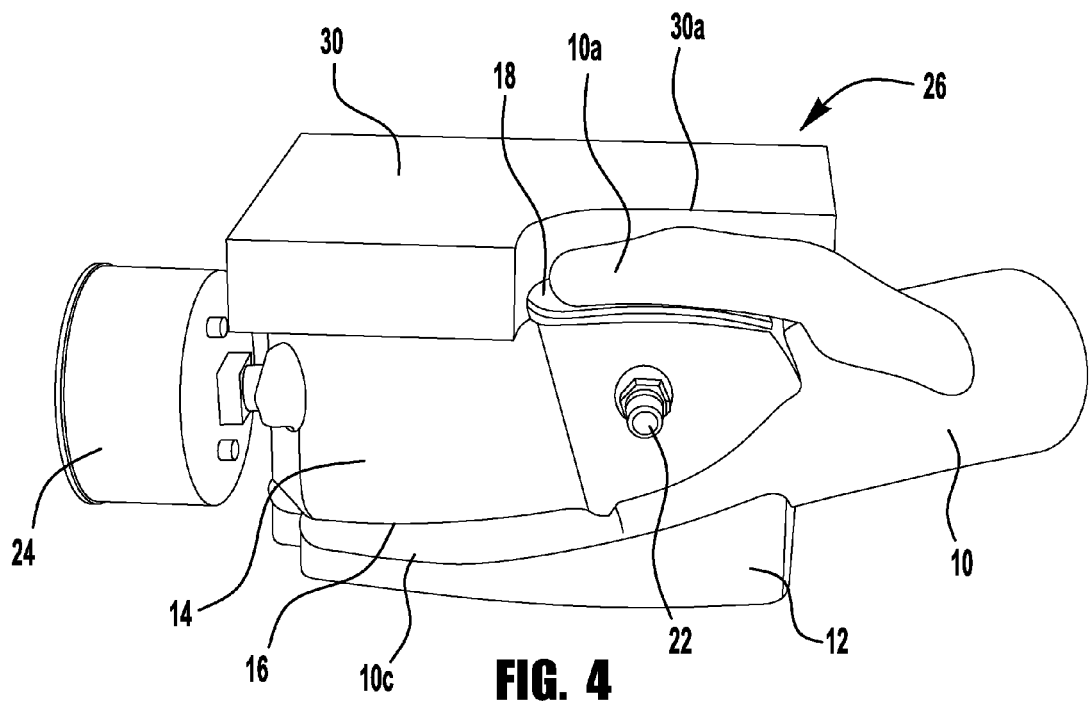
FIG. 4 is a side, three dimensional view of a mannequin hand supported on a cradle, and having top of the weight block disposed on the palm of the mannequin weight block, and a weight disposed on the bottom of the weight block, in accordance with the present invention.

Referring to FIG. 4, there is shown the mannequin hand 10 mounted in the test fixture 26 which includes the hand cradle 12, the patterned weight block 14 and as weight block 30. The back surface 10b of mannequin hand 10 and the back surface of fingers 10c are disposed on the hand cradle 12 so that the mannequin hand is securely held and stabilized with the palm 10d facing upwards. The patterned weight block 14 fits between the palm 10d and the thumb 10a. The expansion chamber 18 is inflated to press against the inner surface of thumb 10a to exert pressure away from the outer surface 20 of weight block 14. The weight block 30, typically of stainless steel, is disposed on the outer surface 20 of the patterned weight block 14 to apply a constant pressure, preferably about 1 psi, against the to the entire mannequin hand, except the thumb 10a—which is achieved with the pressure system 17 alone. Note that the weight 30 has a portion 30a which is shaped to receive the thumb 10a so that no pressure from the weight 30 is exerted against the thumb.

Figure 7:
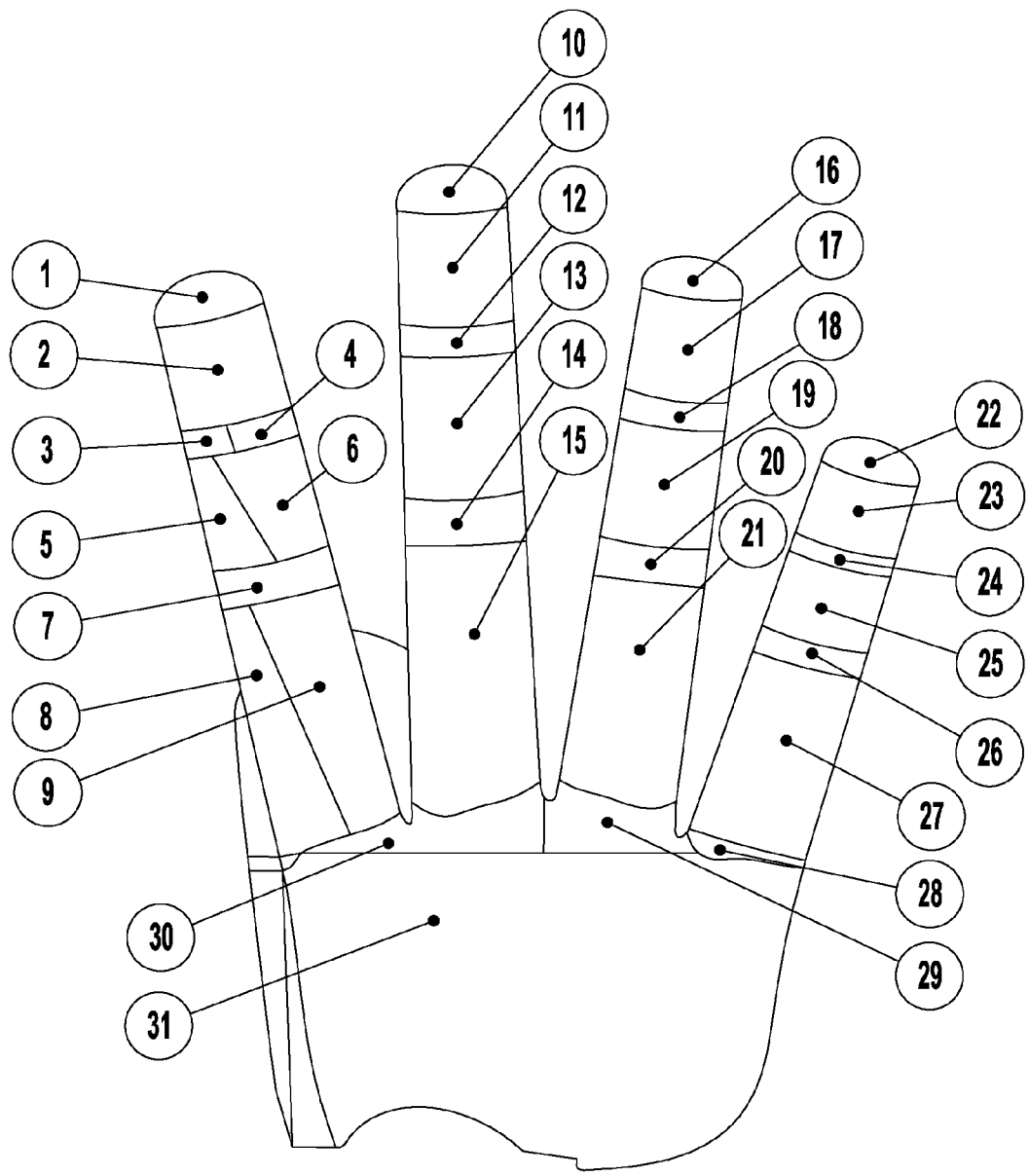
FIG. 7 is a plurality of regions on a mannequin hand for which the effect of pressure is calculated.

The mannequin hand 10 is divided into a plurality of regions, for example 31, as shown in FIG. 7, and mathematically analyzed to determine the pressure at each region. As described above, the weight of the patterned weight block 14 and the rubber expansion chamber 18 are selected to apply a constant pressure, preferably about 1 psi, against the entire mannequin hand 10. The pressure can be adjusted by adding or removing weight, depending on the test needs. The purpose of applying a constant pressure is to ensure that all layers of the glove and absorptive layer, as described hereinafter, are in intimate contact with each other.

Figure 5:
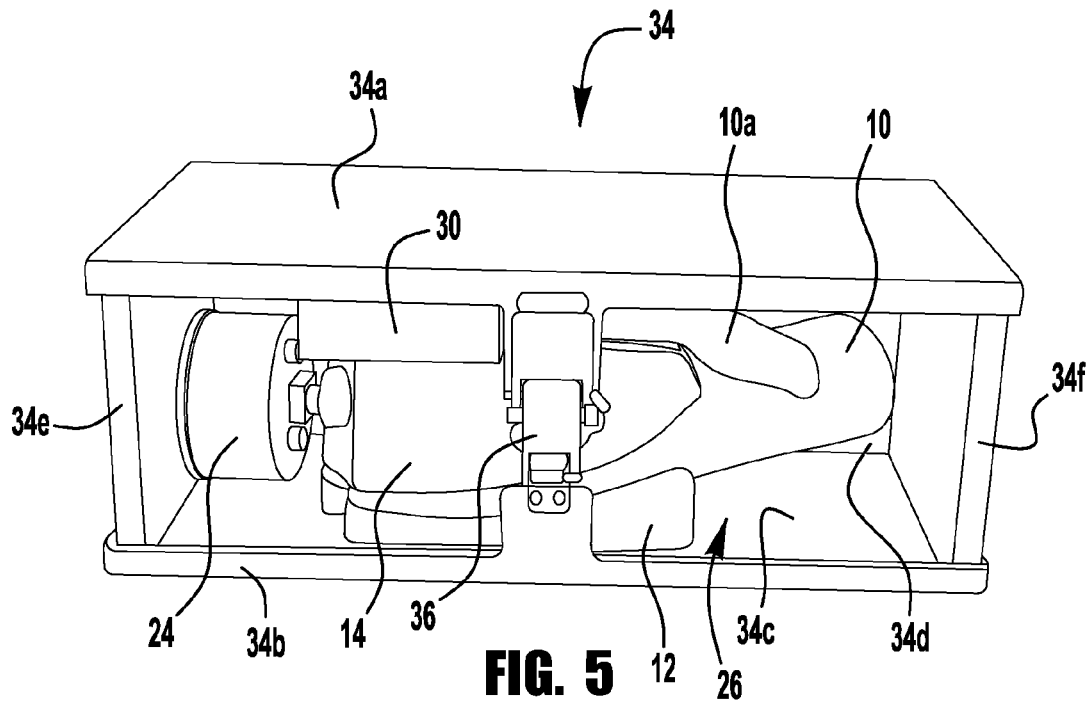
FIG. 5 is a side, three dimensional view of the mannequin hand supported on a cradle, and having top of the weight block disposed on the palm of the mannequin weight block, and a weight disposed on the bottom of the weight block, within a sealed box, in accordance with the present invention.

Referring to FIG. 5, there is illustrated a closed, air tight containment box 34 into which the test fixture 26 including the cradle 12, the mannequin hand 10, the weight block 14 and the weight 30, as shown in FIG. 4, is inserted. The closed, air tight containment box 34 as shown includes a top and bottom cover 34a and 34b, respectively, of stainless steel and front, back and end sidewalls, 34c, 34d, 34e and 34f, respectively, of clear plastic, such as a polycarbonate so that the interior of the containment box 34 can be observed. The top cover 34a can be affixed to the bottom cover 34b with conventional latches 36 on either side of the front and back sidewalk, 34c, and 34d, respectively. The airtight stainless steel and polycarbonate containment box 34 includes rubber gaskets, designed to seal the test fixture 26 within the containment box and prevent cross-contamination during equilibrium in an environmentally controlled chamber (not shown).

The following is the process needed to measure the permeation in a contact scenario.

First, a foil tray (not shown) is placed at the bottom of the containment box 34. This ensures that any residue that might be left in the containment box from a previous experiment does not affect the present experiment. Next, the hand cradle 12 is placed on the foil tray in preparation to receive and support the mannequin hand 10.

Figure 6:
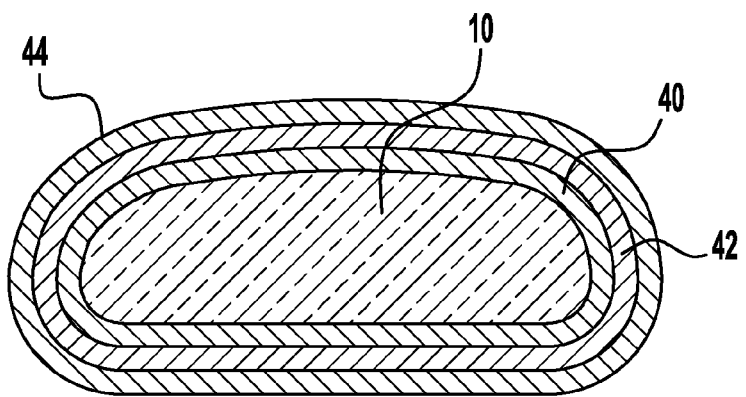
FIG. 6 is a cross sectional view through the mannequin hand encased with an inner, protective glove, a sorptive glove layer 42 and a test glove 40, in accordance with the present invention.

The mannequin hand 10 is expensive to construct. It is accordingly initially protected with a glove 40, as shown in FIG. 6, by forming a protective layer so that the mannequin hand 10 is not compromised during the test by contacting the contaminant being tested. The glove 40 which forms a protective layer can be constructed of nitrile, butyl, neoprene, or other glove material that is appropriate for protection against the contaminant being tested. Once the glove 40 is in place, the open end near the wrist of the mannequin hand is sealed closed by a closure mechanism (not shown) such as crimping, heat sealing or other similar mechanism.

Further as shown in FIG. 6, a sorptive glove layer 42 is placed over the protective glove 40. This sorptive glove layer 42 captures the contamination through the test glove 44. Multiple sorptive layers may be needed, depending on the capacity of the sorptive layer to allow the contaminant being tested to become attached to or absorbed in the sorptive layer. The sorptive glove layer 42 can be made from latex, nitrile, vinyl, or other material that is available as a glove and will sorb the contaminant of interest.

Next, the test glove 44 is placed over the sorptive glove layer 42. The test glove 44 could be any glove to be tested. The test glove 44 is sealed closed at the open end by the wrist of the mannequin hand 10 by a closure mechanism such as crimping, heat sealing or some other similar mechanism.

Continuing, the mannequin hand 10 now encased with the inner, protective glove 40, the sorptive glove layer 42 and the test glove 40 is placed on the cradle 12 already disposed in the foil tray located at the bottom of the containment box 34.

Next, the test glove hand 44 is contaminated with the contaminant of interested at the density and contamination level desired. Standard permeation testing occurs at the 10 $g/m^2$ level. The contaminant should only be applied where there is contact between the patterned weight block 14, the expansion chamber 18 and the test glove 44 on the mannequin hand 10.

A foil liner is next wrapped around the weight block 30. The contaminant of interest can be applied to the area of the foil in contact with the test glove 44. The foil contacts the thumb region of the test glove 40 so as to contaminate the thumb region.

The expansion chamber 18 provided on the outer surface 20 of the patterned weight block 14 can be inflated though the valve stem 22 to a desired pressure which is determined by a pressure gauge 24. The expansion chamber 18, which is disposed between the thumb portion of the test glove 44 and the foil covering the outer surface 20 of the patterned weight block 14 applies the desired pressure of about 1 psi against the thumb portion of the test glove 44.

Continuing, the weight block 30 is placed on the patterned weight block 14 and the air tight containment box 34 is sealed closed as shown in FIG. 5.

Then, the airtight containment box 34 is placed in an environmentally controlled chamber (not shown) and set for the desired time and temperature.

After the fixed amount of time, the air tight containment box 34 is removed from the environmentally controlled chamber and the box unlatched. The weight block 30 and the patterned weight block 14 are removed from the cradle 12. The protective foil on the weight block 14 is disposed of using appropriate hazardous waste disposal procedures.

Continuing, the glove-encased, mannequin hand 10, the cross section of which is shown in FIG. 6 is removed from the cradle 12. The contaminated test glove 10 is removed from the mannequin hand 10 and disposed of, again using appropriate hazardous waste disposal procedures.

The sorptive glove layer(s) 42 are removed from the mannequin hand 10, and extracted in solvent. An appropriate solvent and solvent volume should be chosen with consideration of extraction efficiency of the contaminant from the chosen sorptive layer 42. After extraction for a desired time period, 10 minutes to 4 hours, aliquots are drawn for analysis in order to quantify permeation breakthrough mass in a contact scenario. The advantage of the method as disclosed herein is that the whole glove is combined with contact testing to obtain a true measure of protection in a contact scenario. This is especially useful for testing region difficult to test in fixtures that require flat swatches, such as between the fingers.

Finally, the inner, protective glove layer 40 is removed from the mannequin hand 10 and disposed of using appropriate hazardous waste disposal procedures.

Although the invention has been shown and described with respect to a certain preferred embodiment or embodiments, certain equivalent alterations and modifications will occur to others skilled in the art upon the reading and understanding of this specification and the annexed drawings. In particular regard to the various functions performed by the above described components (assemblies, devices, etc.) the terms (including a reference to a "means") used to describe such components are intended to correspond, unless otherwise indicated, to any component which performs the specified function of the described component (i.e., that is functionally equivalent), even though not structurally equivalent to the disclosed structure which performs the function in the herein illustrated exemplary embodiments of the invention. In addition, while a particular feature of the invention may have been disclosed with respect to only one of several embodiments, such feature may be combined with one or more features of the other embodiments as may be desired and advantageous for any given or particular application.

What is claimed is:

1. A system for testing contact permeation of a glove, comprising:
    a mannequin hand having fingers and a thumb;
    a hand cradle adapted to contact a back surface of the mannequin hand and the fingers to stabilize the hand with a palm of the hand facing outward away from the hand cradle;
    a patterned weight block shaped to fit onto the palm of the mannequin hand and positioned on said palm for applying pressure to the palm, fingers, and thumb of the hand;
    a weight block disposed on an outer surface of the patterned weight block; and
    an air tight containment box to receive the mannequin hand supported by the hand cradle and having the patterned weight block on the palm of the mannequin hand and the weight block disposed on the outer surface of the patterned weight block.

2. The system of claim 1, wherein the air tight containment box is disposed in an environmentally controlled chamber.

3. The system of claim 1, wherein the mannequin hand is constructed of a material selected from the group consisting of plastic or nylon.

4. The system of claim 1, wherein the hand cradle is constructed of a material selected from the group consisting of plastic and nylon.

5. The system of claim 1, wherein the patterned weight block has an inner surface that is shaped to fit snuggly against the contours of the palm and fingers of the mannequin hand.

6. The system of claim 1, wherein the patterned weight block has a pressure system to exert a desired pressure against the thumb of the mannequin hand.

7. The system of claim 6, wherein the pressure system includes a rubber expansion chamber that is disposed between the thumb of the mannequin hand and the outer surface of the weight block.

8. The system of claim 7, wherein a pressure gauge controls the desired pressure of the rubber expansion chamber.

9. The system of claim 7, wherein the weight block exerts a constant pressure against the entire mannequin hand and fingers other than the thumb.

10. A method for testing contact permeation of a contaminant through a glove, comprising:
    providing a mannequin hand with fingers and a thumb;
    placing a protective layer constructed of a material selected from the group consisting essentially of nitrile, butyl, neoprene, or other glove material that is appropriate for the containment of the contaminant being tested, over the mannequin hand;
    placing a sorptive glove layer in place over the protective glove to capture the contamination passing through a test glove,
    placing a test glove over the sorptive glove layer;
    contaminating the test glove with the chemical of interest;
    applying pressure to the palm, fingers, and thumb of the test glove; and
    collecting the contaminant that permeates through the test glove in the sorptive glove layer.

11. The method of claim 10, further including exerting a desired pressure against the thumb of the test glove covering the mannequin hand.

12. The method of claim 10, further including exerting a desired pressure against the entire hand and fingers except for the thumb of the test glove covering the mannequin hand.

13. The method of claim 10, further including placing multiple sorptive layers over the protective glove to fully capture the contaminant being tested.

14. The method of claim 10, further including sealing an open end of the test glove.

15. The method of claim 10, further including placing the mannequin hand with the contaminated test glove over the sorptive glove layer in an air tight containment box.

16. The method of claim 10, further including extracting the contaminant from the sorptive glove layer with a solvent.

17. The method of claim 16, further including extracting the contaminant from the sorptive glove layer with a solvent for a time period of 10 minutes to 4 hours.

18. The method of claim 17, further including drawing aliquots of extracted contaminants for analysis in order to quantify permeation breakthrough mass.

* * * * *